United States Patent [19]

Motier et al.

[11] 4,026,822

[45] May 31, 1977

[54] ZIRCONIUM PHOSPHINE COMPLEX CATALYST

[75] Inventors: John F. Motier, Dolton; Jin Sun Yoo, Riverdale, both of Ill.

[73] Assignee: Atlantic Richfield Company, Philadelphia, Pa.

[22] Filed: July 12, 1974

[21] Appl. No.: 488,134

Related U.S. Application Data

[62] Division of Ser. No. 820,302, April 29, 1969, Pat. No. 3,855,341.

[52] U.S. Cl. .................. 252/429 B; 252/431 D
[51] Int. Cl.² ............................. B01J 31/02
[58] Field of Search .................. 252/429 B, 431 P

[56] References Cited

UNITED STATES PATENTS

| | | | |
|---|---|---|---|
| 2,832,759 | 4/1958 | Nowlin | 252/429 B |
| 2,951,066 | 8/1960 | Coover et al. | 252/429 B |
| 3,051,692 | 8/1962 | Lyons | 252/429 B |
| 3,081,287 | 3/1963 | Coover et al. | 252/429 B |
| 3,379,706 | 4/1968 | Wilke | 252/429 R |
| 3,576,902 | 4/1971 | Bearden et al. | 252/429 B |

*Primary Examiner*—Patrick P. Garvin
*Assistant Examiner*—John P. Sheehan
*Attorney, Agent, or Firm*—John B. Goodman

[57] ABSTRACT

A catalyst composition for the polymerization, including oligomerization and codimerization, of olefins is provided by combining (A) zirconium, (B) a monophosphine electron donor ligand, and (C) a Lewis acid-reducing agent, in molar ratios of (B) to (A) of about 1 to 10:1 and (C) to (A) of about 1 to 40:1. Preferred catalyst components are zirconium acetylacetonate, triphenylphosphine or tri-n-butylphosphine and ethylaluminum sesquichloride. The catalyst composition of this invention may be employed in the dimerization of olefins such as propylene as well as in codimerization reactions, such as the preparation of heptenes from propylene and butenes.

9 Claims, No Drawings

ZIRCONIUM PHOSPHINE COMPLEX CATALYST

This is a division, of application Ser. No. 820,302, filed Apr. 29, 1969 now U.S. Pat. No. 3,855,341. This invention relates to a catalyst composition and its use in the polymerization, including codimerization and oligomerization, of olefins. In particular aspects, the invention relates to a process for the formation of hexenes by dimerization of propylene and a catalyst therefor. In addition, the catalyst of this invention may be employed in codimerization reactions, such as the preparation of heptenes from propylene and butenes. The catalyst may be unsupported or carried by a suitable base.

Numerous catalysts have been disclosed in the prior art as suitable for the preparation of polymeric products of olefins, particularly to form low molecular weight dimers, trimers, tetramers, etc. of such olefins. Normally gaseous olefins such as propylene have, for example, been effectively dimerized using these catalyst systems to produce hexene fractions of varying compositions. The polymeric and oligomeric products produced in such reactions are often valuable in either the petrochemical field or the fuel industry or both. One of the major fractions of dimeric propylenes, 2-methylpentenes, can be utilized, for instance, for the synthesis of isoprene. Another propylene dimerization product, 2,3-dimethylbutene, is useful as a feed for the production of 2,3-dimethylbutadiene which in turn can be used in a multi-step synthesis of pyromellitic anhydride, or can be hydrogenated to yield 2,3-dimethylbutane, useful as an octane-enhancing ingredient in gasoline. The latter compound, for example, has the highest research octane number (103.5) of those paraffins having boiling points up to 140° F.

It has now been found that complexes of zirconium with an organomonophosphine electron donor ligand, when combined with a non-protonic Lewis acid capable of forming a coordination bond with zirconium, and a reducing agent capable of reducing zirconium acetylacetonate to an oxidation state of less than 4 and even to 0, provide a catalyst composition having highly desirable physical and chemical characteristics and, particularly, excellent catalytic activity and selectivity for the polymerization, including codimerization and oligomerization, of low molecular weight olefins. To obtain such compositions, the catalyst-forming reactants can be combined in a molar ratio of electron donor ligand to zirconium of about 1 to 10:1, preferably about 2 to 7:1; and a Lewis acid-reducing agent to zirconium molar ratio of about 1 to 40:1, preferably about 10 to 20:1.

In the preparation of the catalyst composition of the present invention, the zirconium source is provided by compounds of the metal which are at least slightly soluble in some solvent wherein the zirconium-phosphine ligand complex can be formed. Preferred are the weak field ligand complexes, the ligands of which readily serve in solution as transfer agents. Suitable sources of the zirconium can include, for example, hilides, e.g. $ZrCl_4$, $ZrBr_4$, $ZrI_4$; zirconium sulfate; alkoxy derivatives, i.e. $Zr(OR)_4$, where R represents alkyl, aryl, aralkyl, and the like groups; alkoxy zirconium carboxylate, i.e., $(RO)_4ZrOOCR'$ where R and R' are as defined above as R; phosphine complexes, e.g. $Zr[(C_6H_5)_2PC_2H_4P(C_6H_5)_2]X_4$, where X is a halide. Also available as zirconium sources are chelates formed by the zirconium and weak field ligand, such as β-diketones or β-ketocarboxylic acid esters and salts of carboxylic acids. Examples of these types of zirconium sources include β-diketonato zirconium (IV), acetylacetonato zirconium (IV), propylacetonato zirconium (IV), benzoylacetonato zirconium; chelates from β-ketocarboxylic acid esters; salts of saturated monocarboxylic acids, e.g. zirconium formate, zirconium propionate, and the like; salts of corresponding unsaturated monocarboxylic acids, e.g. zirconium acrylate, zirconium vinyl acetate and the like; salts of saturated dicarboxylic acids, e.g. zirconium adipate and the like; salts of corresponding unsaturated dicarboxylic acids, e.g. zirconium muconate and the like; salts of cyclic and aromatic carboxylic acids, e.g. zirconium cyclohexane carboxylate, zirconium phenyl acetate, zirconium benzoate, zirconium phthalates, and the like; and alkoxycarboxylates, e.g. zirconium methoxyacetate and the like. Preferred as a source of zirconium is zirconium acetylacetonate.

The electron donor ligand component employed in preparing the zirconium complex component of the catalyst of the present invention is preferably a triorganophosphine corresponding to the general formula $R_3P$ wherein R is a hydrocarbon radical, e.g. alkyl, aryl, alkaryl, aralkyl and cycloalkyl of from 1 to about 20 carbon atoms, preferably 2 to about 6 carbon atoms, and preferably devoid of olefinic or acetylenic unsaturation; different R groups may, of course, be present in the same phosphine molecule. When the phosphine component contains aromatic groups it is generally preferred that these have mono-cyclic structures, e.g. that the groups be selected from phenyl, alkylphenyl, or phenylalkyl radicals.

The presence of the electron donor ligand component, preferably a triorganophosphine, which apparently can enter into a complex-forming reaction with the zirconium compound, makes for a more active catalyst composition. The phosphine component is monodentate or unidentate, i.e., unifunctional, as regards the phosphorus atom. Use of multifunctional phosphines such as a bis (diphenylphosphino) ethane in place of the unidentate phosphine in the catalyst composition of the present invention has been found, for example, to result in a composition showing no catalytic activity for the dimerization of propylene. Examples of suitable phosphines for the composition of the present invention are triphenylphosphine, trimethylphosphine, tricyclohexylphosphine, tri-n-butylphosphine, tri-n-decylphosphine, tribenzylphosphine, tri-(4-n-butylphenyl) phosphine, and the like. The selection of a particular triorganophosphine may depend upon the polymerization product desired. In the preparation of hexenes by the dimerization of propylene, for example, use of tri-n-butylphosphine normally produces a maximum of dimethylbutenes. Such products would be particulary desired if the hexene fraction were to be used in gasoline, since 2,3-dimethylbutenes possess high octane numbers.

The Lewis acid and the reducing agent functions of our catalyst are preferably supplied in a single compound. As examples of such compounds, there may be mentioned the acidic metal halides which correspond to the general formula:

wherein M is a metallic element of coordination number n whose halides are Lewis acids, X is a halogen having an atomic number of 9 to 53, i.e. fluorine, chlorine, bromine, iodine, R' is hydrocarbyl, e.g. alkyl, of 2 to about 6 carbon atoms any y is a number having a value from greater than o to n. Preferred metallic elements in the above compound include aluminum, magnesium, beryllium, lead, zinc and tin. Examples of suitable such acidic metal halides include alkylaluminum halides including mono-, sesqui-, and dihalides, aluminum trichloride, zinc chloride and stannic chloride. Specific examples of suitable alkylaluminum halides are diethylaluminum chloride, fluoride, iodide, and bromide; ethylaluminum dichloride, ethylaluminum sesquichloride, etc.

Where the particular reducing agent employed in the composition does not also perform as a Lewis acid, it is necessary to separately supply the Lewis acid to the catalyst composition. Examples of reducing agents which are suitable in the preparation of the catalyst composition but which do not perform as Lewis acids therein include trialkylaluminum, monoalkoxydialkylaluminum and dialkylaluminum hydrides wherein the alkyl and alkoxy groups contain up to about 6 carbon atoms. Other examples are Grignard reagents, allyl and alkyl tin complexes, and the like. The reducing agent must be compatible with the Lewis acid and be capable of reducing zirconium acetylacetonate, preferably to an oxidation state lower than 4 and even to 0.

Where the reducing agent doew not also function as a Lewis acid, an additional Lewis acid component can be supplied by a compound which is other than a protonic or hydrogen acid and which is capable of receiving one or more pairs of electrons to form a coordination bond. Lewis acids are well known to the art and are fully defined for example by Noller Chemistry of Organic Compounds, W. B. Saunders, 1951, at pages 233–235, by Stone Chemical Review (1958) at page 101, and by G. N. Lewis, Journal of the Franklin Institute (226–293. Examples of Lewis acids which are not included as a component of a compound which also serves as a reducing agent include boron-trifluoride, boron-trifluoride etherates, e.g. diethyletherate, aluminum trihalides, zinc halides and stannic halides.

The preparation of the overall catalyst composition is preferably conducted by first forming the complex of the electron donor ligand and the zirconium source and then adding to a solution or suspension of that complex, in a suitable organic solvent, the reducing agent and the Lewis acid. Suitable organic solvents for the final catalyst composition are those which are inert to the catalyst and which will not significantly enter into, or deleteriously affect, the eventual polymerization reaction. as specific examples thereof may be mentioned aromatic and aliphatic hydrocarbons and their halogenated, e.g. chlorinated, derivatives. Oxygen-containing solvents are generally to be avoided for this purpose.

Formation of the ligand-zirconium complex may be effected by simply mixing the two reactants in the presence of a suitable solvent for the complexing reaction. The mixing may be done at room temperature or a temperatures as high as about 300° F. The complex usually forms within about 20 to 40 minutes after mixing at elevated temperatures. Suitable solvents for the complex-forming reaction include the same solvents which are suitable for use in the final catalyst composition. A mixture of solvents may also be employed. For example, the ligand-zirconium complex may be formed in chlorobenzene and the Lewis acid-reducing agent added in the form of a solution in toluene. If desired, the complexing may be accomplished in a solvent which is unsuitable for use in the final composition; in this case the resultant complex will first be isolated from the reaction mixture and redissolved, or re-suspended, in a proper solvent which is inert to the final catalyst composition.

Thus, for example, one method of preparing a phosphine-zirconium complex can involve stirring, preferably at room temperature, a mixture of triphenylphosphine, zirconium acetylacetonate and chlorobenzene. After the resulting complex has been formed, ethylaluminum sesquichloride in toluene may then be added directly to the reactant mixture.

The addition to the complex solution of the reducing agent and Lewis acid is preferably conducted in a dry, inert atmosphere, out of the presence of air, for instance in an autoclave. Within a relatively short period of time after the admixing of the components, e.g. about 5 to 15 minutes, an active catalyst composition is formed which may be used to catalyze the polymerization of low molecular weight olefins.

The catalyst compositions of this invention may be used to catalyze the production of liquid polymers, including dimers and oligomers, of mono-ethylenically unsaturated olefinic hydrocarbons of 2 to about 6, or even up to about 8, carbon atoms, as well as monophenyl-or-diphenyl derivatives thereof. By the terms polymerization and polymer it is meant to include herein copolymerization and copolymers as well as homopolymerization and homopolymers, and oligomerization and oligomers, e.g. dimerization and dimers, trimerization and trimer, etc., as well as cross- or co-oligomerization e.g., cross- or co-dimerization, etc. For example, by cross-dimerization, used here as being synonymous with co-dimerization, is meant the addition reaction combining one mole of a first olefin, for instance propylene, with one mole of a second olefin, for instance, butene, to form one mole of a cross-dimer, for instance heptene. By dimerization, on the other hand, is meant the addition reaction which simply combines two moles of a single olefin, for instance propylene, to form the respective dimer, for instance hexene. Polymerization and polymers are the terms here used to embrace all of these reactions and reaction products.

Thus, suitable feeds include, for instance, monoethylenically unsaturated olefins, such as internal- and alpha-olefins, such as ethylene, propylene and butenes; and phenyl-substituted derivatives of the foregoing olefins, such as styrene and 1-phenylbutene-2. The polymers produced by the action of this present catalyst composition will often be of 2 to about 4 monomer units per molecule, i.e. will often range from dimers to tetramers. The catalyst composition has been found, for example, to be especially suitable for the production of hexene fractions by the dimerization of propylene.

Polymerization can be effected by contacting the olefinically-unsaturated feed at an elevated temperature of, for instance, about 100° to 300° F., preferably about 140° to 160° F., which can be maintained by an external heating means. A pressure of about 0 to 600 or more psig, preferably about 250 to 600 psig, is suitable with the catalyst composition of the present invention. Generally, higher pressures and temperatures are favorable for the reaction. The amount of catalyst composition used in the reaction is that sufficient to effect polymerization of the feed, and often is about 0.05 to 5 weight percent, preferably about 0.1 to 1%, of catalyst composition (not including the solvent therefor) based on the weight of olefinic hydrocarbon feed.

The preparation and utilization of the catalyst of the present invention are illustrated by the following examples. Details of reaction conditions, catalyst compositions, and product distribution for these examples are listed in Tables I and II.

EXAMPLE I

A stainless steel autoclave was used as a reactor. Zirconium acetylacetonate in the amount of 2.0 m. moles (millimoles) and triphenylphosphine in the amount of 10.0 m. moles were weighed into the reactor together with 15 ml. of chlorbenzene. The reactor was purged thoroughly with nitrogen and the contents were stirred vigorously fot 15 minutes. Ethylaluminum sesquichloride ($Et_3Al_2Cl_3$) in the amount of 25 m. moles was then added through a septum in the form of a 25 percent solution in toluene. A small amount of toluene (5ml.) was used to wash the $Et_3Al_2Cl_3$ through the delivery line into the reactor. After heating the contents to 125° F. for 15 minutes, 240 ml. of propylene was introduced into the reactor. The temperature of the contents was adjusted to 155° F. A rapid pressure drop (approximately 10 psig/min.) persisted for 45 minutes. The reaction was terminated by cooling the contents to 90° F. and discharging the yellow reaction mixture into a chilled flask. The products were distilled and identified by gas liquid chromatography. Tables I and II list the reaction conditions, catalyst composition and products obtained. The autoclave was immediately recharged with 260 ml. of propylene and the reaction scheme repeated. The results of this recharge and one additional recharge are listed in Table II.

EXAMPLE II

A subsequent set of reactions was run in the manner as in Example I, but tri-n-butylphosphine was substituted for triphenylphosphine. The amounts of the components were the same as the amounts employed in Example I. The reaction conditions, catalyst composition and products of the reactions are listed in Tables I and II.

1. A catalyst comprising a complex of
   A. zirconium acetylacetonate;
   B. an electron donor ligand phosphine of the formula $R_3P$ wherein each R is a hydrocarbon of up 20 carbon atoms, with
   C. a combination of a reducing agent capable of reducing zirconium acetylacetonate to an oxidation state of less than 4 and a non-protonic Lewis acid capable of forming a coordination bond with zirconium selected from a compound represented by the formula

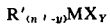

wherein
   R' is alkyl of 2 to about 6 carbon atoms, X is chlorine, M is a metallic element of coordination number n' whose halides are Lewis acids selected from aluminum magnesium, beryllium, lead, zinc and tin and y is a number having a value of greater than 0: the molar ratio of (B) to (A) being about 2 to 7:1 and the molar ratio of (C) to (A) being about 10 to 20:1, said components (C) and (A) being combined to reduce zirconium represented by (A) to an oxidation state of less than 4, and form a coordination bond with (A).

2. A catalyst of claim 1 wherein M is aluminum.

3. A catalyst of claim 1 wherein each R is selected from alkyl, aryl, alkaryl, aralkyl and cycloalkyl.

4. A catalyst of claim 2 wherein each R is selected from alkyl, aryl, alkaryl, aralkyl and cycloalkyl.

5. A catalyst of claim 1 wherein each R is selected from alkyl, aryl and cycloalkyl of 2 to about 6 carbon atoms.

6. A catalyst of claim 2 wherein each R is selected from alkyl, aryl and cycloalkyl of 2 to about 6 carbon atoms.

7. A catalyst of claim 4 wherein each R is selected from alkyl, aryl and cycloalkyl of 2 to about 6 carbon atoms.

8. A catalyst of claim 5 wherein R is selected from alkyl and phenyl.

9. A catalyst of claim 7 wherein R is selected from alkyl and phenyl.

* * * * *

UNITED STATES PATENT OFFICE
CERTIFICATE OF CORRECTION

Patent No. 4,026,822    Dated May 31, 1977

Inventor(s) John F. Motier et al.

It is certified that error appears in the above-identified patent and that said Letters Patent are hereby corrected as shown below:

Column 3, line 28, "doew" should read --- does ---.

After last line in Column 5, add the attached Tables I & II. respectively.

Signed and Sealed this

Twenty-seventh Day of September 1977

[SEAL]

Attest:

RUTH C. MASON
Attesting Officer

LUTRELLE F. PARKER
Acting Commissioner of Patents and Trademarks

TABLE II

Distribution of Products

| Example No. | IA | IB | IC | IIA | IIB |
|---|---|---|---|---|---|
| Component (1) | | | Weight % | | |
| $4\text{-}MC_5^{=1}$, $3\text{-}MC_5^{=1}$ | 2.12 | 3.36 | 4.37 | 2.38 | 5.01 |
| $4\text{-}MC_5^{=2C}$ | 8.98 | 11.20 | 13.77 | 8.70 | 15.84 |
| $2,3\text{-}DMC_4^{=1}$, $4\text{-}MC_5^{=2T}$ | 31.35 | 28.71 | 29.35 | 46.70 | 56.82 |
| $C_6^{=1}$, $2\text{-}MC_5^{=1}$ | 14.67 | 13.34 | 13.61 | 12.46 | 9.69 |
| $C_6^{=3C}$ | 4.01 | 3.04 | 2.66 | 1.96 | 1.03 |
| $2\text{-}MC_5^{=2}$ | 13.34 | 11.82 | 10.90 | 6.32 | 3.38 |
| $C_6^{=2}$, $3\text{-}MC_5^{=2C}$ | 17.10 | 17.13 | 16.43 | 15.32 | 7.41 |
| $4,4\text{-}DMC_5^{=2T}$ | 4.23 | 4.41 | 4.28 | 1.91 | 0.83 |
| $C_8^=\text{-}C_9^=$ | 2.25 | 5.48 | 0.51 | 2.14 | - |
| Yield, % | 65.3 | 62.2 | 66.7 | 69.0 | 64.0 |

Note:

(1) $4\text{-}MC_5^{=1}$ is 4-methylpentene-1; $4,4\text{-}DMC_5^{=2T}$ is 4,4-dimethylpentene-2 (trans); etc.

TABLE I

Catalyst Composition and Reaction Conditions

| | | | Catalyst Composition | | | | | Reaction Conditions | | |
|---|---|---|---|---|---|---|---|---|---|---|
| Example No. | Run No. | Feed $C_3^=$, g | $Zr(acac)_4$ m mole | $R_3P$ m mole | R in $R_3P$ | $Et_3Al_2Cl_3$ m mole | Solvent (1) g. | Pressure psig | Temp. °F. | Time Hr |
| I | A | 125 | 2.0 | 10.0 | ∅ | 25 | 33 | 150-450 | 155 | 1 |
|   | B | 135 | 2.0 | 10.0 | ∅ | 25 | 33 | 300-600 | 150 | 1-1 |
|   | C | 135 | 2.0 | 10.0 | ∅ | 25 | 33 | 150-230 | 155 | 1-1 |
| II | A | 131 | 2.0 | 10.0 | n-Bu | 25 | 38 | 80-650 | 150 | 1-1 |
|   | B | 137 | 2.0 | 10.0 | n-Bu | 25 | 38 | 130-600 | 153 | 1-1 |

Note:

(1) A mixture of chlorobenzene and toluene.